US008518653B2

(12) United States Patent
Takkinen et al.

(10) Patent No.: US 8,518,653 B2
(45) Date of Patent: Aug. 27, 2013

(54) DETECTION OF CANNABIS USE (75) Inventors: Kristiina Takkinen, Espoo (FI); Hans Söderlund, Espoo (FI); Timo Pulli, Helsinki (FI)

(73) Assignee: Teknologian Tutkimuskeskus VTT, Espoo (FI)

( * ) Notice: Subject to any disclaimer, the term of this patent is extended or adjusted under 35 U.S.C. 154(b) by 126 days.

(21) Appl. No.: 12/994,805

(22) PCT Filed: Jun. 5, 2009

(86) PCT No.: PCT/FI2009/050481
§ 371 (c)(1),
(2), (4) Date: Nov. 26, 2010

(87) PCT Pub. No.: WO2009/150295
PCT Pub. Date: Dec. 17, 2009

(65) Prior Publication Data
US 2011/0086364 A1    Apr. 14, 2011

(30) Foreign Application Priority Data
Jun. 12, 2008   (FI) .................................. 20085579

(51) Int. Cl.
C07K 16/42   (2006.01)
C07H 21/04   (2006.01)
C12P 21/08   (2006.01)
G01N 33/53   (2006.01)
G01N 33/536  (2006.01)
G01N 33/543  (2006.01)
G01N 33/563  (2006.01)
G01N 33/577  (2006.01)
G01N 33/94   (2006.01)
C07K 16/16   (2006.01)

(52) U.S. Cl.
USPC ........... 435/7.1; 435/7.8; 435/7.92; 435/7.94; 435/69.7; 435/70.21; 435/91.1; 435/471; 435/320.1; 435/971; 435/975; 436/507; 436/512; 436/518; 436/536; 436/548; 436/164; 436/172; 436/802; 436/816; 530/388.9; 530/391.1; 530/391.3; 530/866; 530/867; 536/23.53

(58) Field of Classification Search
USPC ............. 435/7.1, 7.8, 7.92, 7.94, 69.7, 70.21, 435/91.1, 471, 320.1, 971, 975; 436/507, 436/512, 518, 548, 164, 172, 802, 816, 536; 530/388.9, 389.3, 391.1, 391.3, 866, 867; 536/23.53
See application file for complete search history.

(56) References Cited

U.S. PATENT DOCUMENTS

| 4,670,383 | A  | * | 6/1987  | Baier et al.    | 435/7.92 |
| 5,480,792 | A  | * | 1/1996  | Buechler et al. | 435/6.16 |
| 6,326,159 | B1 |   | 12/2001 | Ullman et al.   |          |
| 7,749,712 | B2 | * | 7/2010  | Pulli et al.    | 435/7.1  |

FOREIGN PATENT DOCUMENTS

| WO | 87/07147       | * | 12/1987 |
| WO | 2004/046733 A1 |   | 6/2004  |
| WO | 2007/141278 A2 |   | 12/2007 |

OTHER PUBLICATIONS

Lo Muzio, L., et al., "Saliva as a Diagnostic Matrix for Drug Abuse", International Journal of Immunopathology and Pharmacology, vol. 18, No. 3, pp. 567-573, (2005).
Hemmila, M., et al., "Homogeneous Time-Resolved Fluroimmunoassay of Thyroxin in Serum", Clin. Chem. vol. 34, No. 11, pp. 2320-2322, (1988).
Kintz P., et al., "Detection of Cannabis Use in Drivers with the Drugwipe Device and by GC-MS after Intercept Device Collection", J. Anal Toxicol. vol. 7, pp. 724-727, Oct. 29, 2005.
Kerrigan, S., et al., "Comparison of ELISAs for Opiates, Methamphetamine, Cocaine Metabolite, Benzodiazepines, Phencyclidine, and Cannabinoids in Whole Blood and Urine", Clinical Chemistry 47:3, pp. 540-547, (2001).
Akahori, Y., et al., Immunoglobulin Lambda Light Chain VLJ Region [*Homo sapiens*],Unpublished, database GenBank, accession BAC01824, (Feb. 7, 2002).http://www.ncbi.nlm.nih.gov/protein/21669599?report=genpept&lo..., 3 pages.
Raharjo, T. J, et al., "Methods for the Analysis of Cannabinoids in Biological Materials: a Review", Phytochemical Analysis, vol. 15, pp. 79-94, (2004).
Pulli, T., et al., "One-Step Homogeneous Immunoassay for Small Analytes", Anal. Chem, vol. 77, pp. 2637-2642, (2005).
Ullman, E. F., et al., "Anti-immune complex antibodies enhance affinity and specificity of primary antibodies", Pro. Natl. Acad. Sci. USA, vol. 90, pp. 1184-1189, Feb. 1993.

* cited by examiner

*Primary Examiner* — Gail R Gabel
*Assistant Examiner* — James L Grun
(74) *Attorney, Agent, or Firm* — Nath, Goldberg & Meyer; Joshua B. Goldberg (57) ABSTRACT

A binding partner, especially an antibody fragment that specifically recognizes an antigen-antibody immune complex between anti-THC and THC (tetrahydrocannabinol), is disclosed. The binding partner facilitates a non-competitive homogenous immunoassay for detection of *cannabis* use. A test kit comprising the binding partner is also described. Preferably the immunoassay is applied for roadside testing of saliva from suspected drivers.

17 Claims, 3 Drawing Sheets

Anti-THC T3 Fab

Anti-THC T3 Fab light chain
DIVLTQSPTTMAASPGEKITITCSASSSISSNYLHWYQQKPG
FSPKLLIYRTSNLASGVPARFSGSGSGTSYSLTIGT
MEAEDVATYYCQQGSSIPLTFGAGTKLELKRADAAPTVSI
FPPSSEQLTSGGASVVCFLNNFYPKDINVKWKIDGSERQN
GVLNSWTDQDSKDSTYSMSSTLTLTKDEYERHNSYTCEAT
HKTSTSPIVKSFNRNEC anti-THC T3 Fab VH-CH1
AEVKLVESGGGLVKPGGSLKLSCAASGFTFNNYVMV
WLRQTPEKRLEWVASISRGGSTYYPDSVKGRF
TISRDNARNILNLQMSSLRSEDTAMYYCVR**GTTIVAG
D**VWGAGTTVTVSSAKTTPPSVYPLAPGSAAQTN
SMVTLGCLVKGYFPEPVTVTWNSGSLSSGVHTFPAV
LQSDLYTLSSSVTVPSSTWPSETVTCNVAHPASS
TKVDKKIVPRDCG

CDR1
*CDR2*
<u>CDR3</u>

Fig. 1

Anti-T3+THC immune complex Fab 104

Fab 104 light chain:
NFMLTQPHSVSESPGKTVTISCTGSSGSIASNY
VQWYQQRPGSAPTTVIY*EDNQRPS*GVPDRFS
GSIDSSSNSASLTISGLKTEDEADYYCQSYDSS
NQVFGGGTKLTVLGQPKAAPSVTLFPPSSEEL
QANKATLVCLISDFYPGAVTVAWKADSSPVKA
GVETTTPSKQSNNKYAASSYLSLTPEQWKSHK
SYSCQVTHEGSTVEKTVAPAECS

Fab 104 Fab VH-CH1-6His-Tag
QVQLVQSGTEVKKPGATVKISCKFSGDNFIDYYMHWV
KQAQGKGLEWLG*LVDLGDGQTIY*AEKFHGRGTITADS
SRDTAYMELSSLRSEDTAVYYCAAAKAYRQGVMDVW
GQGTLVTVSSASTKGPSVFPLAPSSKSTSGGTAALGCL
VKDYFPEPVTVSWNSGALTSGVHTFPAVLQSSGLYSLS
SVVTVPSSSLGTQTYICNVNHKPSNTKVDKKAEPKSCH
HHHHH

CDR1
*CDR2*
CDR3

Fig. 3

SEQUENCE LISTING

<160> NUMBER OF SEQ ID NOS: 4

<210> SEQ ID NO 1
<211> LENGTH: 215
<212> TYPE: PRT
<213> ORGANISM: Murinae gen. sp.
<220> FEATURE:
<221> NAME/KEY: DOMAIN
<222> LOCATION: (1)..(108)
<223> OTHER INFORMATION: VL
<220> FEATURE:
<221> NAME/KEY: MISC_FEATURE
<222> LOCATION: (24)..(35)
<223> OTHER INFORMATION: CDR1
<220> FEATURE:
<221> NAME/KEY: MISC_FEATURE
<222> LOCATION: (51)..(57)
<223> OTHER INFORMATION: CDR2
<220> FEATURE:
<221> NAME/KEY: MISC_FEATURE
<222> LOCATION: (90)..(98)
<223> OTHER INFORMATION: CDR3
<220> FEATURE:
<221> NAME/KEY: DOMAIN
<222> LOCATION: (109)..(215)
<223> OTHER INFORMATION: CL

<400> SEQUENCE: 1

Asp Ile Val Leu Thr Gln Ser Pro Thr Thr Met Ala Ala Ser Pro Gly
1               5                   10                  15

Glu Lys Ile Thr Ile Thr Cys Ser Ala Ser Ser Ser Ile Ser Ser Asn
            20                  25                  30

Tyr Leu His Trp Tyr Gln Gln Lys Pro Gly Phe Ser Pro Lys Leu Leu
        35                  40                  45

Ile Tyr Arg Thr Ser Asn Leu Ala Ser Gly Val Pro Ala Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Ser Ile Pro
                85                  90                  95

Leu Thr Phe Gly Ala Gly Thr Lys Leu Glu Leu Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215

<210> SEQ ID NO 2
<211> LENGTH: 221
<212> TYPE: PRT
<213> ORGANISM: Murinae gen. sp.
<220> FEATURE:

```
<221> NAME/KEY: DOMAIN
<222> LOCATION: (1)..(118)
<223> OTHER INFORMATION: VH
<220> FEATURE:
<221> NAME/KEY: MISC_FEATURE
<222> LOCATION: (27)..(36)
<223> OTHER INFORMATION: CDR1
<220> FEATURE:
<221> NAME/KEY: MISC_FEATURE
<222> LOCATION: (51)..(66)
<223> OTHER INFORMATION: CDR2
<220> FEATURE:
<221> NAME/KEY: MISC_FEATURE
<222> LOCATION: (99)..(107)
<223> OTHER INFORMATION: CDR3
<220> FEATURE:
<221> NAME/KEY: DOMAIN
<222> LOCATION: (119)..(221)
<223> OTHER INFORMATION: CH

<400> SEQUENCE: 2

Ala Glu Val Lys Leu Val Glu Ser Gly Gly Gly Leu Val Lys Pro Gly
 1               5                  10                  15

Gly Ser Leu Lys Leu Ser Cys Ala Ala Ser Gly Phe Thr Phe Asn Asn
                20                  25                  30

Tyr Val Met Val Trp Leu Arg Gln Thr Pro Glu Lys Arg Leu Glu Trp
            35                  40                  45

Val Ala Ser Ile Ser Arg Gly Gly Ser Thr Tyr Tyr Pro Asp Ser Val
    50                  55                  60

Lys Gly Arg Phe Thr Ile Ser Arg Asp Asn Ala Arg Asn Ile Leu Asn
65                  70                  75                  80

Leu Gln Met Ser Ser Leu Arg Ser Glu Asp Thr Ala Met Tyr Tyr Cys
                85                  90                  95

Val Arg Gly Thr Thr Ile Val Ala Gly Asp Val Trp Gly Ala Gly Thr
            100                 105                 110

Thr Val Thr Val Ser Ser Ala Lys Thr Thr Pro Pro Ser Val Tyr Pro
    115                 120                 125

Leu Ala Pro Gly Ser Ala Ala Gln Thr Asn Ser Met Val Thr Leu Gly
130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly
    210                 215                 220

<210> SEQ ID NO 3
<211> LENGTH: 216
<212> TYPE: PRT
<213> ORGANISM: Homo sapiens
<220> FEATURE:
<221> NAME/KEY: DOMAIN
<222> LOCATION: (1)..(111)
<223> OTHER INFORMATION: VL
<220> FEATURE:
<221> NAME/KEY: MISC_FEATURE
<222> LOCATION: (23)..(35)
<223> OTHER INFORMATION: CDR1
<220> FEATURE:
<221> NAME/KEY: MISC_FEATURE
<222> LOCATION: (51)..(57)
```

<223> OTHER INFORMATION: CDR2
<220> FEATURE:
<221> NAME/KEY: MISC_FEATURE
<222> LOCATION: (93)..(100)
<223> OTHER INFORMATION: CDR3
<220> FEATURE:
<221> NAME/KEY: DOMAIN
<222> LOCATION: (112)..(216)
<223> OTHER INFORMATION: CL

<400> SEQUENCE: 3

Asn Phe Met Leu Thr Gln Pro His Ser Val Ser Glu Ser Pro Gly Lys
1               5                   10                  15

Thr Val Thr Ile Ser Cys Thr Gly Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Gln Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205

Thr Val Ala Pro Ala Glu Cys Ser
    210                 215

<210> SEQ ID NO 4
<211> LENGTH: 229
<212> TYPE: PRT
<213> ORGANISM: Homo sapiens
<220> FEATURE:
<221> NAME/KEY: DOMAIN
<222> LOCATION: (1)..(120)
<223> OTHER INFORMATION: VH
<220> FEATURE:
<221> NAME/KEY: MISC_FEATURE
<222> LOCATION: (29)..(35)
<223> OTHER INFORMATION: CDR1
<220> FEATURE:
<221> NAME/KEY: MISC_FEATURE
<222> LOCATION: (50)..(60)
<223> OTHER INFORMATION: CDR2
<220> FEATURE:
<221> NAME/KEY: MISC_FEATURE
<222> LOCATION: (99)..(109)
<223> OTHER INFORMATION: CDR3
<220> FEATURE:
<221> NAME/KEY: DOMAIN
<222> LOCATION: (121)..(223)
<223> OTHER INFORMATION: CH
<220> FEATURE:

```
<221> NAME/KEY: MISC_FEATURE
<222> LOCATION: (224)..(229)
<223> OTHER INFORMATION: 6His-Tag

<400> SEQUENCE: 4

Gln Val Gln Leu Val Gln Ser Gly Thr Glu Val Lys Lys Pro Gly Ala
1               5                   10                  15

Thr Val Lys Ile Ser Cys Lys Phe Ser Gly Asp Asn Phe Ile Asp Tyr
            20                  25                  30

Tyr Met His Trp Val Lys Gln Ala Gln Gly Lys Gly Leu Glu Trp Leu
        35                  40                  45

Gly Leu Val Asp Leu Gly Asp Gly Gln Thr Ile Tyr Ala Glu Lys Phe
    50                  55                  60

His Gly Arg Gly Thr Ile Thr Ala Asp Ser Ser Arg Asp Thr Ala Tyr
65                  70                  75                  80

Met Glu Leu Ser Ser Leu Arg Ser Glu Asp Thr Ala Val Tyr Tyr Cys
                85                  90                  95

Ala Ala Ala Lys Ala Tyr Arg Gln Gly Val Met Asp Val Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Ala Glu Pro Lys Ser Cys His
    210                 215                 220

His His His His His
225
```

DETECTION OF CANNABIS USE

This is a National Phase Application filed under 35 U.S.C. 371 as a national stage of PCT/FI2009/050481, with the filing date of Jun. 5, 2009 an application claiming the benefit to the Finnish Application No. 20085579, filed on Jun. 12, 2008, the entire content of each of which is hereby incorporated by reference in its entirety.

The official copy of the sequence listing is submitted electronically via EFS-Web as an ASCII formatted sequence listing with a file name "2080 700 PC.ST25 sequence_listing.txt", created on Nov. 23, 2010, and is filed concurrently with the specification. The sequence listing contained in this ASCII formatted document is part of the specification and is herein incorporated by reference in its entirety.

FIELD OF THE INVENTION

The invention provides means for enhancing immunoassays for detecting *cannabis* use. In particular the invention relates to a binding partner, especially an antibody fragment that is capable of binding an immune complex between tetrahydrocannabinol (THC) and an anti-THC-antibody. The invention is also directed to a test-kit comprising the binding partner, and the use of said binding partner for detecting *cannabis* use. Further the invention relates to an immunoassay, wherein said binding partner is used. Still further the invention is directed to a polynucleotide encoding said binding partner, and a host cell capable of expressing it.

TECHNICAL BACKGROUND OF THE INVENTION

Drug abuse is a severe threat especially to traffic safety, and therefore a number of assays have been developed for convenient testing of drugs of abuse. Many of the tests are immunoassays, and they are mostly competitive immunoassays, which generally are less specific than non-competitive ones. Kerrigan and Phillips have e.g. compared 12 commercially available ELISAs (enzyme linked immunosorbent assays) for opiates, methamphetamine, benzodiazepines, cocaine metabolite, phencyclidine and cannabinoids in whole blood and urine. (Kerrigan S., & Phillips, W., 2001 Clinical Chemistry 47(3):540-547). The test format was competitive immunoassay, and the results were not fully satisfying giving some false results and undesired cross-reactivity.

Drugs of abuse may be assayed not only from blood or urine, but also from saliva, which is the test matrix of choice for roadside testing. Lo Muzio et al. tested a commercial rapid immunological screening test for detecting drugs in urine, and compared two biological matrixes: a nonconventional one, saliva, and a traditional one, urine. They found that saliva specimens were negative in the immunological test for *cannabis*, THC, benzodiazepines, and tricyclic antidepressants although gas-chromatography-mass-spectrometry (GC-MS) analysis revealed low concentrations thereof, and concluded that the test kit must be improved before being used with saliva (Lo Muzio L., et al., 2005, Int J Immunopathol Pharmacol. 18(3):567-573).

WO 2004/046733 discloses a non-competitive immunoassay for assaying small analytes such as drugs of abuse. The assay uses a first antibody specific for the analyte, and a second antibody specific for an immune complex (IC) between the first antibody and the analyte to improve the sensitivity and specificity of an assay. The anti-IC antibody used was obtained from a naive human antibody fragment phage display library by preincubating the display phages with bound first antibody to sort out those binding to the first antibody as such, whereafter unbound phages were separated and incubated with a mixture of analyte and immobilized first antibody to select phages that bind to the immune complex formed between the immobilized first antibody and analyte, but not to the antibody as such. Very good results for determining morphine in saliva were obtained.

$\Delta$9-tetrahydrocannabinol ($\Delta$9-THC) is the parental drug of *cannabis*, and it is rapidly metabolized to 11-nor-$\Delta$9-THC-COOH or 11-OH-$\Delta$9-THC that may be determined in urine. Thus the use of *cannabis* is preferably detected by assaying $\Delta$9-THC in saliva, which is a better indication of recent use than when the metabolites are detected in urine. However, it has turned out to be difficult to develop a quick-test for this analyte, and the test kits on the market are not sensitive enough.

U.S. Pat. No. 6,326,159 and Ullman et al., 1993. Proc. Natl. Acad. Sci 90:1184-1189 describe an immunoassay using anti-IC-antibodies for enhancing the affinity and specificity of primary antibodies. In these papers, a secondary anti-IC antibody, which binds primary anti-analyte antibody that is combined with the analyte, but which does not bind the primary antibody or the analyte alone, has been developed. An antibody that recognizes an immune complex of an antibody to tetrahydrocannabinol (THC) is disclosed. The anti-IC antibody was obtained using an affinity labeled anti-THC antibody as immunogen and selecting an anti-IC antibody the binding of which was enhanced by the presence of $\Delta$9THC. Some cross-reactivity with e.g. THC-metabolites was observed, which is undesirable in forensic drug analysis. The antibodies were prepared by conventional hybridoma technique, which render them too big for application in homogenous immunoassays.

Kintz P. et al. tested a commercial drug device for testing drugs in saliva, and compared the results with GC-MC analysis results, and found that the test device identified only one driver exposed to THC, whereas 18 drivers tested positive with GC-MC. They concluded that a current limitation of the use of this specimen for roadside testing is the absence of a suitable immunoassay that detects the parent compound (THC) in sufficiently low concentrations (Kintz P., et al., 2005. J Anal Toxicol. 29(7):724-727).

The current immunoassays for determining *cannabis* use are not satisfactory i.a. due to low specificity and sensitivity. Thus there is still a need for an easy, rapid and reliable drug test for *cannabis* use, which may be used e.g. for roadside testing and preferably for analyzing oral fluid samples, which are non-invasive, easy to perform, and may be achieved under close supervision. The present invention meets at least part of these needs.

SUMMARY OF THE INVENTION

The present invention provides a novel reagent, which facilitates rapid and reliable detection of *cannabis* use. The reagent is a protein capable of specifically recognizing an immune complex formed between cannabinoid and anti-cannabinoid. More specifically the present invention provides a binding partner comprising the complementary determining regions (CDRs) of an antibody light chain and heavy chain, wherein said light chain regions have the amino acid sequences of amino acids 23-35, 51-57, and 93-100 of SEQ ID NO:3, and said heavy chain regions have the amino acid sequences of amino acids 29-35, 50-60 and 99-109 of SEQ ID NO:4.

The invention further provides a test-kit comprising the binding partner, and the use of the binding partner for detecting a cannabinoid in a body sample taken from a person to be tested for having used *cannabis*. Due to high specificity and sensitivity and preferably small size the binding partner is especially suitable for a non-competitive homogenous immunoassay that may be used e.g. by the road for testing saliva of drivers suspected of *cannabis* use.

Still further the invention provides an immunoassay for detecting an analyte in a sample taken from a body, whereby the sample is reacted with a reagent pair comprising a first binding partner that specifically binds to the analyte, and a second binding partner that specifically binds to the complex of the analyte and the first binding partner, and determining the binding of the second binding partner to said complex, thus indicating the presence of the analyte in the sample, wherein said analyte is a cannabinoid, and said second binding partner comprises the complementary determining regions (CDRs) of an antibody light chain and heavy chain, wherein said light chain regions have the amino acid sequences of amino acids 23-35, 51-57, and 93-100 of SEQ ID NO:3, and said heavy chain regions have the amino acid sequences of amino acids 29-35, 50-60 and 99-109 of SEQ ID NO:4.

Yet in addition the invention provides a polynucleotide encoding the binding partner, and a host cell capable of expressing the binding partner. The polynucleotide is DNA or RNA.

Advantageous embodiments of the invention are set forth in the dependent claims.

Other objects, details and advantages of the invention will become apparent from the following drawings, detailed description and examples.

DETAILED DESCRIPTION

Cannabinoid is a general name of terpenphenolic molecules found in *cannabis* plants *Cannabis sativa*. More generally it encompasses a group of molecules, which are structurally related to tetrahydrocannabinol (THC) and which bind to the cannabinoid receptor. THC is the major psychoactive cannabinoid of *cannabis*, and it is synonymous with Δ9-tetrahydrocannabinol (Δ9-THC) and D9-tetrahydrocannabinol (D9-THC), which all may be used interchangeably herein. THC is metabolized in the body to i.a. 11-nor-D9-THC-COON and 11-OH-D9-THC, which are examples of other cannabinoids. The binding partner of the invention recognizes specifically an immune complex between THC and anti-THC, whereby the reaction with the metabolites is significantly lower.

The binding partner of the invention may be used in a sandwich assay for detecting THC in a sample, whereby the sample is reacted with a reagent pair comprising a first binding partner that specifically binds to THC, and a second binding partner, which is capable of specifically recognizing an immune complex between THC and anti-THC, and which is the binding partner of the invention. Binding of the second binding partner to the immune complex between the first binding partner and THC indicates the presence of THC in the sample.

"Binding partner" as used herein is usually a protein or polypeptide, such as antibodies including antibody fragments that have the desired binding properties. An antibody is an immunoglobulin molecule and it can belong to any of classes IgG, IgM, IgE, IgA or IgD; IgG and IgM being the most frequently used. Preferably the binding partners are antibody fragments comprising the ligand-binding site, such as Fab, or scFv fragments. The fragment known as the Fab fragment (fragment antigen binding) consists of the variable and constant domain of an immunoglobulin light chain covalently attached by a disulfide bridge to the variable and first constant domain of an immunoglobulin heavy chain. Fv (variable domain) means the variable regions of the immunoglobulin molecule that are responsible for the ligand binding. ScFv (single chain Fv) means a molecule wherein the variable domains of the heavy and light chain of an antibody are linked by a peptide to form a single polypeptide chain synthesized from a single mRNA molecule. The variable regions of an immunoglobulin heavy chain and light chain are together responsible for the ligand binding. Ligand is the substance to which the binding partner binds, in connection with antibodies it is an antigen or a hapten.

The binding partners are conveniently prepared using a recombinant phage display binding partner library e.g. as described in WO 2004/046733. When the first binding partner has been selected for, it is complexed with its ligand and this complex is used to select for the second binding partner from a recombinant library. The first binding partner without the ligand is used as contraselection. The second binding partner should only recognise complexes, not free first binding partner nor free antigen to any significant extent.

A phage display antibody library may be constructed by cloning immunoglobulin domains coding cDNAs into an appropriate phage display vector. DNA encoding for millions of variants of antibody fragments is batch-cloned into the vector as part of the phage coat protein. Large libraries containing millions of antibody fragments with different specificities can be obtained by transforming the vectors in bacteria. Cultivation of the bacteria leads to the expression of phages displaying antibody fragments on their surface. The gene for the displayed antibody is carried in the phage genome, thus linking genotype with phenotype. The physical linkage between the displayed protein and its DNA allows screening of vast numbers of variants of the protein, each linked to its corresponding DNA, by a simple in vitro selection procedure called panning. In its simplest form, panning is carried out by incubating the pool of phage-displayed variants with the ligand of interest that has been immobilized on a carrier, washing away unbound phage, and eluting specifically bound phage by disrupting the binding to the ligand. The eluted phage is then amplified in vivo. The process is repeated several times, resulting in stepwise enrichment of the phage pool in favour of the tightest binding sequences. After about 3 to 6 rounds of selection and amplification, the best clones are sequenced and transformed into a host cell for further expression. The host cell may be a eucaryotic or procaryotic cell e.g. a yeast, animal, plant or insect cell or bacterial cell. It may even be a hybridoma cell, which after transformation produces a recombinant monoclonal antibody. The recombinant binding partner or at least part of it may also be produced synthetically.

The reagent pair comprising a first binding partner recognizing cannabinoid, and a second binding partner recognizing an immune complex between cannabinoid and said first binding partner makes a non-competitive sandwich assay for cannabinoid feasible. The sandwich can be detected by all the standard immunoassays. One partner may be immobilized on a carrier, such as a microtiter well or a bead. A sandwich is formed in the presence of analyte and the other binding partner. The sandwich may be detected e.g. by using secondary antibodies or by labeling at least one of the binding partners. The label can be any conventional label, such as a radioactive label, an enzyme, or a fluorescent compound. The assay can be e.g. ELISA or FIA.

A great advantage of a reagent pair comprising the binding partner of the present invention is that it enables a homogenous immunoassay, i.e. an immunoassay that is carried out in solution. The avoidance of immobilizing and washing steps makes the assay extremely simple. The homogenous assay provides an excellent and convenient tool for on-site tests e.g. to be used by the police in raiding drivers etc. The immunoassay provided by the invention is up to ten times more sensitive than the competitive assays presently on the market. The sample to be analysed may be any body fluid sample such as blood, serum or urine, but preferably it is an oral fluid such as saliva. The analyte is preferably THC.

A preferred homogenous immunoassay is one based on fluorescence resonance energy transfer (FRET), for review see Szöllösi J. et al., 1998, Communications in Clinical Cytometry, 34:159-179. In FRET, energy from a molecular fluorophore (donor) is excited to a high-energy state and transferred to another fluorophore (acceptor) via intermolecular dipole-dipole coupling. This is possible only if the distance between the donor and the acceptor is short (10-100 Å) and the fluorescence spectrum of the donor and the absorption spectrum of the acceptor partially overlap. The energy transfer is then detected as a change in fluorescence. Often time-resolved fluorescence is utilized (Hemmilä I. et al., 1988, Clin. Chem. 34:2320-2322).

FRET may be applied to the present invention by labeling the two binding partners, which preferably are antibody fragments, with fluorophores that form a FRET donor-acceptor pair. When the binding partners and the analyte are small the fluorophores come into very close proximity, and a measurable FRET signal is obtained.

Alternatively the immunoassay for *cannabis* use may be for example a conventional sandwich test in microtiter wells or a lateral flow-test.

The binding partner of the invention may be included in a test-kit, which may further contain any other reagents needed for the assay together with instructions for use. Preferably the test-kit contains also a first binding partner for binding the analyte. More preferably said binding partner comprises the complementary determining regions (CDRs) of an antibody light chain and heavy chain, wherein said light chain regions have the amino acid sequences of amino acids 24-35, 51-57, and 90-98 of SEQ ID NO:1, and said heavy chain regions have the amino acid sequences of amino acids 27-36, 51-66 and 99-107 of SEQ ID NO:2. Preferably the test-kit comprises reagents for carrying out a non-competitive, homogenous assay such as e.g. reagents needed for a TR-FRET test. The kit may further comprise reaction solutions, buffers, washing solutions and detecting means, such as labels and optionally a fluorometer.

The performance of the test may be such that the reagents are in the well of a microtiter plate and dilution series of sample is added. In a preferred mode for e.g. police field use, the reagents are in dry form in a vessel. Saliva is added, which dissolves the reagents and the result can be read without further processes.

Preferably the test kit comprises reagents for assaying multiple drugs of abuse, such as reagents for assaying e.g. morphine, codeine, heroin, amphetamine, metamphetamine, cocaine, barbiturates and benzodiazepines. In that case the test-kit may comprise multiple reagent pairs physically separated from each other e.g. in the form of a microarray, whereby the multiple drugs may be tested simultaneously from a single saliva sample.

The binding partner of the invention comprises three CDRs of an antibody light chain having the sequence of SEQ ID NO:3, and three CDRs of an antibody heavy chain having the sequence of SEQ ID NO:4. According to one embodiment of the invention the binding partner comprises the whole variable region i.e. the ligand-binding portion of said light chain (VL) and heavy chain (VH). It may thus contain amino acids 1-111 of SEQ ID NO:3 and amino acids 1-120 of SEQ ID NO:4. In particular said binding partner comprises the amino acid sequences of SEQ ID NO:3 and NO:4. Correspondingly the first binding partner may comprise the whole variable region of SEQ ID NO:1, and of SEQ ID NO:2, i.e. amino acids 1-108 of SEQ ID NO:1 and amino acids 1-118 of SEQ ID NO:2. Especially it comprises the amino acid sequences of SEQ ID NO:1 and NO:2. Minor variations or modifications of any one of the sequences or subsequences set forth in the description and claims are still within the scope of the invention provided that they do not affect the binding activity of the proteins. Such variations and modifications especially include conservative amino acid substitutions.

The invention is illustrated by the following non-limiting examples.

Example 1

Development of Anti-THC Fab

Mice were immunized with THC conjugated BSA (Fitzgerald) in Freund's adjuvant, and serum samples were tested after second booster, and the mouse showing the best response against the antigen in direct ELISA was selected to be the source of an antibody phage display library. An antibody fragment phage display library was constructed, THC-specific phages were enriched, and the Fab gene fragment of individual clones were isolated, expressed and characterized as described in WO 2004/046733. Anti-THC T3 Fab was chosen for further assay.

Figure 1:
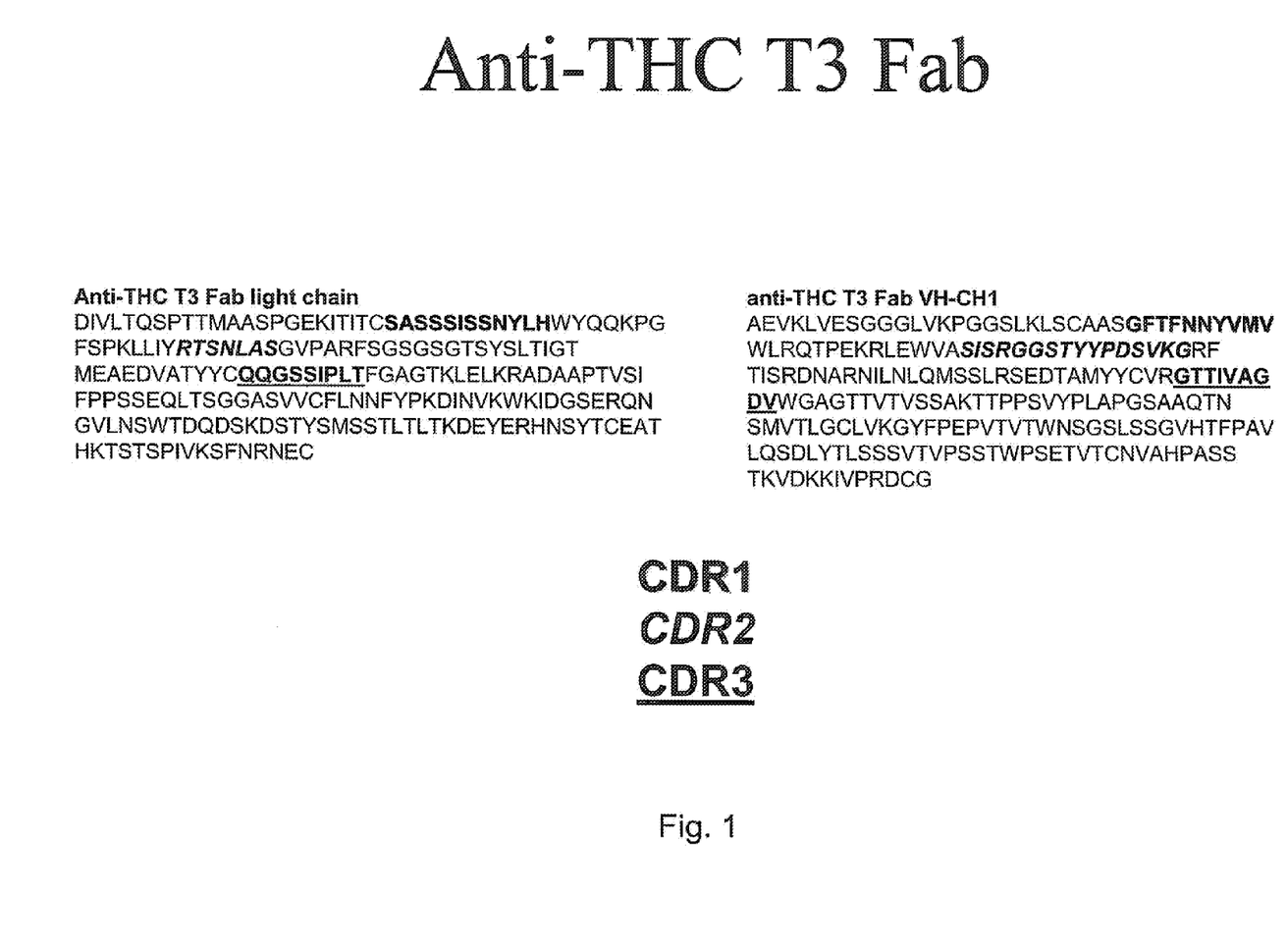
FIG. 1 shows the amino acid sequences of the anti-THC T3 Fab light chain (SEQ ID NO:1), and anti-THC T3 Fab VH-CH1 heavy chain (SEQ ID NO:2). The three complementary determining regions CDR1, CDR2 and CDR3 of each of said immunoglobulin chains are indicated.
Figure 2:
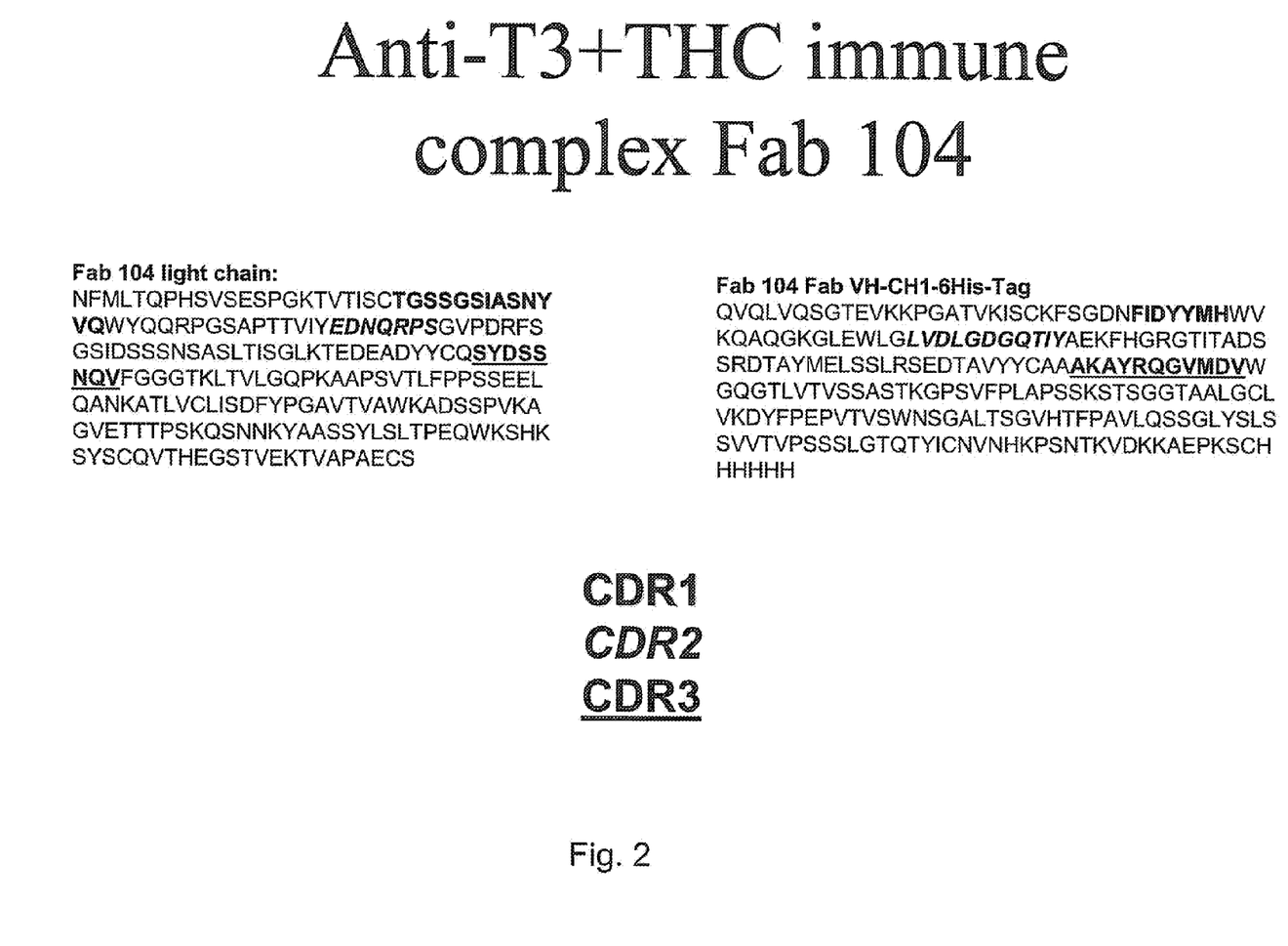
FIG. 2 shows the amino acid sequences of the anti-T3+THC immune complex Fab 104 light chain (SEQ ID NO:3), and anti-T3+THC immune complex Fab 104 heavy chain (SEQ ID NO:4). The three complementary determining regions CDR1, CDR2 and CDR3 of each of said immunoglobulin chains are indicated.

The amino acid sequence of anti-THC T3 Fab light chain is set forth as SEQ ID NO:1, and anti-THC T3 Fab VH-CH1 chain is set forth as SEQ ID NO:2. CDR1, CDR2, and CDR3 of the Fab light chain correspond to amino acids 24-35, 51-57 and 90-98 of SEQ ID NO:1. CDR1, CDR2 and CDR3 of the Fab heavy chain correspond to amino acids 27-36, 51-66 and 99-107 of SEQ ID NO:2. Amino acids no 1-108 of SEQ ID NO:1 represent the variable region of the light chain, and amino acids no 1-118 of SEQ ID NO:2 represent the variable region of the heavy chain. Amino acids no 109-215 of SEQ ID NO:1 represent the constant region of the mouse kappa light chain, and amino acids no 119-221 of SEQ ID NO:2 represent the mouse constant $CH_1$ region of the heavy chain. The amino acid sequences of anti-THC T3 Fab are also shown in FIG. 1.

Example 2

Development of an Anti-Immune Complex Antibody to the Immune Complex of Anti-THC Fab and THC Selection of the Immune Complex Specific Antibody from a Naive Human scFv Phage Display Library T3 Fab fragment was biotinylated with ImmunoPure Sulfo-NHS-LC-Biotin Kit (Pierce). Biotinylated antibody was purified and buffer was changed to PBS with Econo-Pac 10DG Columns (Bio-Rad, CA, USA). 200 µl of a naive human scFv phage display library (Kappa or Lambda light chain) in BSA/PBS was preincubated with 10 µl of streptavidin coated magnetic beads (Dynal, M-280) and 0.5 µl of biotinylated T3 Fab for over night at +4° C. The naive human scFv phage display library was constructed from pooled lymphocytes of 50 healthy individuals. The size of the library was estimated to be $1 \times 10^8$ clones. The naive human scFv phage display library contains the IgM specific $V_H$-genes combined either with the kappa or lambda specific $V_L$-genes. Unbound phages were separated from the beads and 100 µl of them was incubated with 100 ng of THC, 500 ng of biotinylated T3 Fab, and 5 µl of streptavidin coated magnetic beads for 1 h at RT on a shaker. The background for the selection procedure was implemented in a similar way but omitting the THC from the binding reaction. Magnetic beads were washed five times with 0.5 ml of PBS and bound phages were eluted with 100 µl of HCl (pH 2.2) for 30 min. The eluted phages were neutralized with 1M Tris and *E. coil* XL1-Blue cells were infected. Cells were grown and phages were purified as described in WO 2004/046733. After three panning rounds enrichment was seen, when the amount of eluted phages was compared to the amount of eluted phages from the background control well. The enrichment of specific binders to the immune complex, formed by T3 Fab and THC, was also clearly seen in a phage ELISA when the eluted phage pools from the selection rounds were tested and by analyzing individual scFv phage clones.

Characterization of Individual Clones

Individual scFv phage clones binding specifically to T3+THC complex were picked, sequenced, expressed and tested. Clone 104 was chosen for further examination. Since scFvs are prone to aggregation during expression and purification, the immune complex specific clone 104 was converted to a Fab fragment by cloning the gene regions of human lambda light chain and IgG1 CH1 constant regions to the $V_L$ and $V_H$ genes, respectively. A C-terminal tag containing six histidine residues was inserted into the C-terminus of the CH1 for immobilized metal affinity chromatography (IMAC) purification. 104 Fab fragment was cloned into the expression vector pKKtac and the sequence was verified. The amino acid sequence of anti-T3+THC immune complex Fab 104 light chain is set forth as SEQ ID NO:3 and of the Fab VH-CH1-6His-Tag region as SEQ ID NO:4. Amino acids no 1-111 of SEQ ID NO:3 represent the variable region of the light chain, and amino acids no 1-120 of SEQ ID NO:4 represent the variable region of the heavy chain. Amino acids no 112-216 of SEQ ID NO:3 represent the constant region of the human lambda light chain, and amino acids no 121-223 of SEQ ID NO:4 represent the constant region of the human heavy chain $CH_1$ region. The six histidine residues at the C-terminus of the heavy chain constant region facilitate the purification of the Fab fragment by immobilized metal affinity chromatography (IMAC).

Expression and Purification of 104 Fab

The expression vector of the 104 Fab fragment was transformed into the *E. coli* production strain RV308. Cells were inoculated into 25 ml of TB medium (yeast extract 12 g/l, Soy peptone 24 g/l, KH2PO4 2.31 g/l, K2HPO4 12.54 g/l, glycerol 5 g/l, pH 7.1) with 100 µg/ml ampicillin and 2% glucose and were incubated over night at +37° C. on a shaker. From the overnight culture a 6 ml inoculate was added into two erlenmeyer bottles containing 300 ml of TB with 100 µg/ml of ampicillin. Cells were incubated at +37° C. on a shaker until the $OD_{600}$ was 4 after which 0.3 ml of 1M IPTG and 100 µg/ml of ampicillin were added into the culture and the incubation was continued over night at +30° C. on a shaker. The supernatant of the culture medium was used for the purification of the 104 Fab fragment. Cells were centrifuged at 4000 g for 20 min at 4° and the supernatant was poured into a clean flask. The supernatant was treated with 2 mg/ml of DNaseI to remove residual chromosomal DNA for one hour at +37° C. Since the expressed Fab 104 has a 6xHis-tag in its C-terminus, it could be purified by immobilized metal affinity chromatography (IMAC). The Fab 104 was purified by $Ni^{2+}$ Chelating Sepharose (Amersham Pharmacia Biotech). The purity of Fab 104 was checked with SDS-PAGE.

Example 3

A Homogenous Time Resolved Fluorescent Resonance Energy Transfer (TR-FRET) Immunoassay for THC The anti-THC Fab fragment T3 was labeled with europium by LANCE Eu-W1024 ITC chelate Kit (Wallac). The buffer of the labeled T3 was changed to 50 mM Tris, pH 7.8, 0.9% NaCl. The anti-T3+THC immune complex Fab fragment 104 was labeled with Alexa Fluor 647 by Alexa Fluor Protein Labeling kit (Molecular Probes, Inc.).

Figure 3:
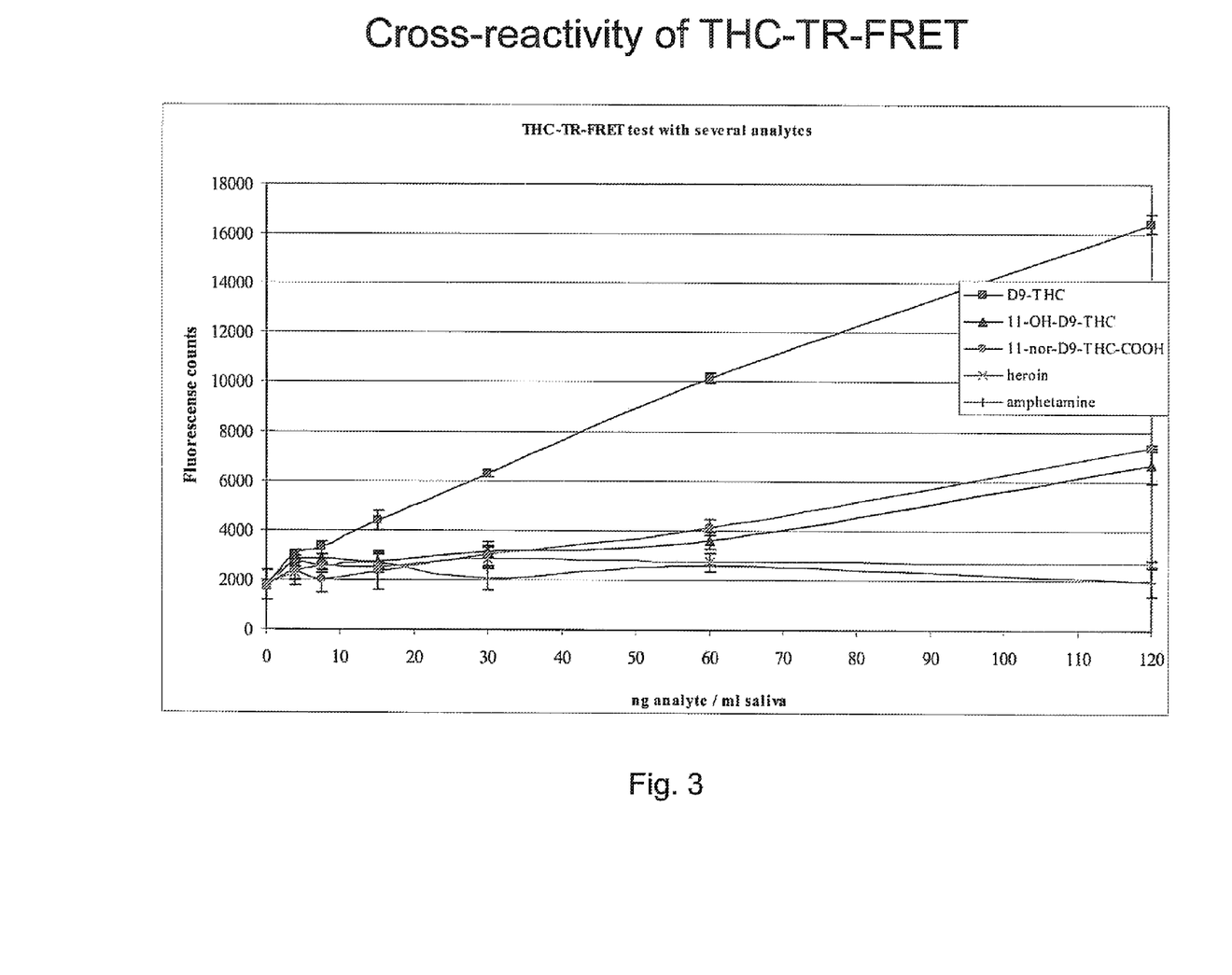
FIG. 3 shows THC TR-FRET test results obtained with the combination of anti-THC T3 Fab and anti-T3+THC immune complex Fab 104 for various drugs and drug metabolites.

1 µg of Eu labeled anti-THC T3 Fab and 1.5 µg of Alexa Fluor 647 labeled anti-immune complex Fab 104 were added to microtiter wells in 60 µl of saliva. 40 µl saliva samples spiked with 0, 3.75, 7.5, 15, 30, 60 and 120 ng/ml of the following drugs: D9-THC, 11-OH-D9-THC, 11-nor-D9-THC-COOH, heroin and amphetamine were added to the wells. After short mixing, the time resolved fluorescence resonance energy transfer (TR-FRET) was measured by Victor V fluorometer (Perkin Elmer Wallac). The results are shown in FIG. 3.

Saliva sample spiked with THC is giving a high fluorescent value, whereas the THC metabolites are giving significantly lower fluorescence values, and heroin and morphine gave fluorescent values close to the background fluorescence detected from the control (labelled T3 and 104 fragments without any added drug). Fab 104 binds the immune complex formed between T3 and THC with extremely high specificity and sensitivity. The test is capable of detecting THC far below the cut-off level (20 ng/ml in saliva) of the quick tests currently in the market.

While one strategy for providing reagents and assays of the invention has been described, numerous variations and modifications will become apparent to the person skilled in the art.

The invention claimed is:

1. An isolated binding partner comprising the complementary determining regions (CDRs) of an antibody light chain and heavy chain, wherein said light chain regions have the amino acid sequences of amino acids 23-35, 51-57, and 93-100 of SEQ ID NO:3, and said heavy chain regions have the amino acid sequences of amino acids 29-35, 50-60 and 99-109 of SEQ ID NO:4.

2. The binding partner according to claim 1, which is an antibody fragment.

3. The binding partner according to claim 2, wherein the antibody fragment comprises amino acids 1-111 of SEQ ID NO:3, and amino acids 1-120 of SEQ ID NO:4.

4. The binding partner according to claim 2, wherein the antibody fragment is Fab 104 comprising SEQ ID NO:3 and SEQ ID NO:4.

5. The binding partner according to claim 1, which specifically recognizes an immune complex between tetrahydrocannabinol (THC) and anti-THC.

6. A test-kit comprising the binding partner of claim 1.

7. The test-kit according to claim 6, further comprising another binding partner comprising the complementary determining regions (CDRs) of an antibody light chain and heavy chain, wherein said light chain regions have the amino acid sequences of amino acids 24-35, 51-57, and 90-98 of SEQ ID NO:1, and said heavy chain regions have the amino acid sequences of amino acids 27-36, 51-66 and 99-107 of SEQ ID NO:2.

8. The test kit according to claim 7, wherein the two binding partners are labeled with fluorophores.

9. An isolated polynucleotide encoding the binding partner of claim 1.

10. An isolated host cell that has been transformed with an isolated polynucleotide encoding the binding partner of claim 1 and being capable of expressing the binding partner of claim 1.

11. A method for detecting cannabinoid in a body sample taken from a person to be tested for having used cannabis, comprising:
    reacting the body sample with a reagent pair comprising a first binding partner that specifically binds to a cannabinoid in the body sample to form a complex and a second binding partner that specifically binds to the complex; and determining the binding of the second binding partner to the complex thereby indicating presence of the cannabinoid in the body sample, wherein said first binding partner comprises the complementary determining regions (CDRs) of an antibody light chain and heavy chain, wherein said light chain regions have the amino acid sequences of amino acids 24-35, 51-57, and 90-98 of SEQ ID NO:1, and said heavy chain regions have the amino acid sequences of amino acids 27-36, 51-66 and 99-107 of SEQ ID NO:2, and said second binding partner is the binding partner according to claim 1.

12. The method according to claim 11, wherein the cannabinoid is THC.

13. An immunoassay for detecting a cannabinoid in a sample taken from a body, comprising:

reacting the sample with a reagent pair comprising a first binding partner that specifically binds to the cannabinoid to form a complex, and a second binding partner that specifically binds to the complex; and determining the binding of the second binding partner to the complex, thereby indicating presence of the cannabinoid in the sample, wherein said first binding partner comprises the complementary determining regions (CDRs) of an antibody light chain and heavy chain, wherein said light chain regions have the amino acid sequences of amino acids 24-35, 51-57, and 90-98 of SEQ ID NO:1, and said heavy chain regions have the amino acid sequences of amino acids 27-36, 51-66 and 99-107 of SEQ ID NO:2, and said second binding partner comprises the complementary determining regions (CDRs) of an antibody light chain and heavy chain, said light chain regions having the amino acid sequences of amino acids 23-35, 51-57, and 93-100 of SEQ ID NO:3, and said heavy chain regions having the amino acid sequences of amino acids 29-35, 50-60 and 99-109 of SEQ ID NO:4.

14. The immunoassay of claim 13, which is a non-competitive, homogenous immunoassay.

15. The immunoassay of claim 14, wherein the non-competitive homogenous immunoassay is a time resolved fluorescent resonance energy transfer (TR-FRET) assay.

16. The immunoassay of claim 13, wherein the sample to be analyzed is selected from the group consisting of blood, urine, and oral fluid.

17. The immunoassay of claim 13, wherein the sample is saliva and the cannabinoid is tetrahydrocannabinol (THC).

\* \* \* \* \*